United States Patent [19]

Chandrachood et al.

[11] Patent Number: 5,777,245

[45] Date of Patent: Jul. 7, 1998

[54] PARTICLE DISPERSING SYSTEM AND METHOD FOR TESTING SEMICONDUCTOR MANUFACTURING EQUIPMENT

[75] Inventors: Madhavi Chandrachood; Steve G. Ghanayem, both of Sunnyvale; Nancy Cantwell, Milpitas, all of Calif.; Daniel J. Rader; Anthony S. Geller, both of Albuquerque, N. Mex.

[73] Assignee: Applied Materials, Inc., Santa Clara, Calif.

[21] Appl. No.: 710,216

[22] Filed: Sep. 13, 1996

[51] Int. Cl.$^6$ .......................... G01N 19/00; G01N 15/02
[52] U.S. Cl. ..................... 73/865.9; 73/37; 73/865.5
[58] Field of Search ................. 73/865.5, 865.9, 73/37, 38

[56] References Cited

U.S. PATENT DOCUMENTS

| | | | |
|---|---|---|---|
| 4,220,499 | 9/1980 | Hughes, Jr. et al. | 356/335 X |
| 4,225,385 | 9/1980 | Hughes, Jr. et al. | 73/863.81 X |
| 4,764,758 | 8/1988 | Skala | 356/37 X |
| 4,967,608 | 11/1990 | Yost | 73/865.5 X |
| 5,037,202 | 8/1991 | Batchelder et al. | 356/338 X |
| 5,196,997 | 3/1993 | Kutaberg et al. | 364/152 |
| 5,298,967 | 3/1994 | Wells | 356/338 X |
| 5,522,933 | 6/1996 | Geller et al. | 118/723 E |
| 5,553,496 | 9/1996 | Nishiyama et al. | 73/865.5 X |

OTHER PUBLICATIONS

*Patent Abstracts of Japan* Abs Grp P1338, vol. 16, No. 155 Abs Pub Date Arp. 16, 1992 (4–6437) "Particulate Measuring System".

*Patent Abstracts of Europe* "Method and Apparatus for Tuning Fields for Plasma Processing Using Corrected Electrode" Abstract of EP 663682 dated Jul. 19, 1995.

*Primary Examiner*—Thomas P. Noland
*Attorney, Agent, or Firm*—Fenwick & West LLP

[57] ABSTRACT

The system and method prepare a gas stream comprising particles at a known concentration using a particle disperser for moving particles from a reservoir of particles into a stream of flowing carrier gas. The electrostatic charges on the particles entrained in the carrier gas are then neutralized or otherwise altered, and the resulting particle-laden gas stream is then diluted to provide an acceptable particle concentration. The diluted gas stream is then split into a calibration stream and the desired output stream. The particles in the calibration stream are detected to provide an indication of the actual size distribution and concentration of particles in the output stream that is supplied to a process chamber being analyzed. Particles flowing out of the process chamber within a vacuum pumping system are detected, and the output particle size distribution and concentration are compared with the particle size distribution and concentration of the calibration stream in order to determine the particle transport characteristics of a process chamber, or to determine the number of particles lodged in the process chamber as a function of manufacturing process parameters such as pressure, flowrate, temperature, process chamber geometry, particle size, particle charge, and gas composition.

3 Claims, 3 Drawing Sheets

PARTICLE DISPERSING SYSTEM AND METHOD FOR TESTING SEMICONDUCTOR MANUFACTURING EQUIPMENT

RELATED CASES

The subject matter of this application is related to the subject matter of U.S. Pat. No. 5,522,933 entitled "Particle Free Microchip Processing", issued Jun. 4, 1996, and to the subject matter of pending patent application Ser. No. 08/537, 192 entitled "Reduction of Particle Deposition on Substrates Using Temperature Gradient Control," filed on Sep. 29, 1995 by D. Rader, et al.

FIELD OF THE INVENTION

This invention relates to apparatus and method for analyzing semiconductor processing equipment, and more particularly to a particle-dispersing system and method for studying particulate contamination in systems such as those used in semiconductor processing equipment.

BACKGROUND OF THE INVENTION

Particulate contamination in manufacturing semiconductor components is a significant problem. A single particle deposited at a critical point on an integrated circuit can render the entire circuit non-functional. As geometries become smaller and circuits become larger and more densely distributed on substrates, the sensitivity to particulate contamination increases.

Many critical operations in semiconductor processing are carried out in processing chambers which perform depositions or etching operations. A wafer placed in the process chamber is typically subjected to a gas flow at a reduced pressure. The gas may contain material to be deposited on the wafer, or may contain chemicals for etching exposed areas on the wafer. Particulate contamination of the carrier gas, or of the material being deposited, or of the process chamber itself can cause undesirable depositions of particles on the wafer.

Particle detectors can be used to detect particles in a process chamber by monitoring the gas pumped from the process chamber for particles. This type of contamination detection scheme is based on the assumption that particles in the deposition system must leave via the vacuum system connected to an outlet port of the processing chamber. These detectors are commonly used to measure a particle performance of the process chamber and to detect when the particle performance in the process chamber deviates from a base line. The operating conditions in the process chamber greatly affect the transport of contaminants. Under certain operating conditions, contaminants may undesirably settle in the process chamber and thereby reduce the base-line particle count measured by such particle detector.

One known technique for calibrating the particle transport of a process chamber introduces particulates within a liquid carrier into the processing chamber. While this technique provides a known concentration of particles, it also introduces into the process chamber a solvent which may damage the chamber and which may alter the conditions in the process chamber relative to the actual operating conditions during normal processing.

SUMMARY OF THE INVENTION

Accordingly, the present invention provides an improved particle dispersement system and method for use in studying transport of particle contamination in semiconductor manufacturing systems. Such particle dispersement system according to the present invention can also be used to calibrate and optimize the use of particle detectors in a semiconductor manufacturing system. The apparatus of the present invention provides an output gas stream comprising well-characterized particles at a known concentration. The apparatus includes a particle disperser and a charge-altering device for moving particles from a reservoir of particles into a flowing gas stream in which electrostatic charges on the particles can be adjusted. The resulting gas stream containing uniformly dispersed and charge-adjusted particles is diluted to provide an acceptable particle concentration. The gas stream with diluted concentration of dispersed particles is then split into a calibration stream and a desired output stream. The particles in the calibration stream are counted to determine the actual size distribution and concentration of particles in the desired output stream. The pressure of the output stream is adjusted to the pressure of the semiconductor manufacturing equipment being analyzed. The output stream is then supplied to the semiconductor manufacturing equipment. A particle counter disposed in an outlet port of the semiconductor manufacturing equipment detects exiting particles, and associated computer analysis of the data assesses the particle transport characteristics of the equipment being analyzed.

DETAILED DESCRIPTION OF THE INVENTION

Figure 1:
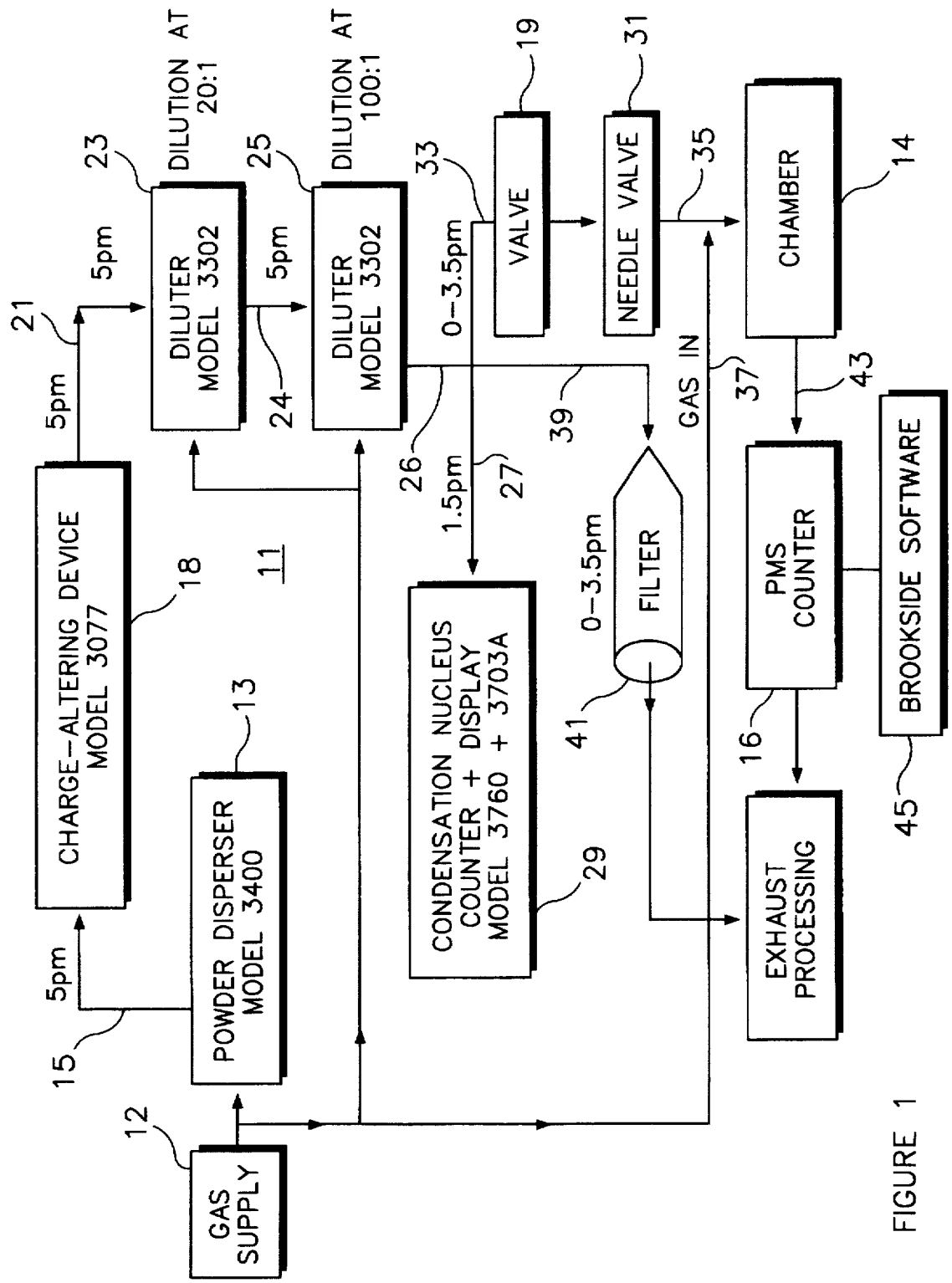
FIG. 1 is a block schematic diagram of a particle dispensing system according to the present invention.

Referring now to the block schematic diagram of FIG. 1, the particle dispersing system 11 according to the present invention provides a calibrated, variable source of particles of known size to the input of a process chamber 14, the output of which is monitored by a particle counter 16. Specifically, particles of an inorganic material such as silicon dioxide of a known size are screened for selected sizes within the range, for example, 0.15 to 5.0 µm, to form a dry powder of dielectric material, and are dispersed into a stream of flowing carrier gas from gas supply 12 by a conventional powder disperser 13 (e.g., model 3400 disperser manufactured by TSI, Inc.). The disperser 13 utilizes a fluidized bed of particles to disperse the particles from a particle reservoir into the stream 15 of a carrier gas such as nitrogen or argon. The particles are preferably silicon dioxide rather than latex or polystyrene spheres for superior thermal stability during passage through the process chamber 14 under operating conditions of elevated temperature. The dry powder of silicon dioxide particles within the selected range of particle sizes is entrained in the gas stream 15 flowing, for example, at the rate of about 5 liters per minute, and with a particle concentration within the range, for example, 10–100 mg/cubic meter.

The particles so dispersed commonly acquire an electrostatic charge, and such electrostatic charge is adjusted or removed by a charge-altering device 18 (e.g., a model 3077 neutralizer manufactured by TSI, Inc.). Charge-altering device 18 may utilize a krypton-85 source as a beta-ray emitter to ionize the carrier gas in stream 15 and thereby adjust or neutralize charges on the entrained particles.

Alternatively, other charge-altering devices 18 may be used which utilize polonium as an alpha-ray emitter to ionize the flowing carrier gas and thereby adjust or remove electrostatic charges on the entrained particles. Alternatively, charges on particles may also be adjusted or removed by passing the particles between two electrodes operated on D.C. or alternating voltage.

The particular type of dry powder utilized depends upon the process conditions under which process chamber 14 is analyzed. A wide variety of processing conditions, however, may be explored utilizing silicon dioxide particles. These particles are commercially available in a wide range of particle sizes and are well characterized by weight and shape, are stable at high temperatures, and are easily removed from the process chamber 14 after calibration, for example, with isopropyl alcohol.

The concentration of particles in the output stream 21 of charge-altering device 18 is too high to be useful in analyzing the behavior of process chamber 14 under semiconductor processing conditions. Hence, the concentration of particles in the output stream 21 of charge-altering device 18 is diluted by a factor of approximately 2000 by diluters 23, 25. Since the required dilution factor is significantly higher than can be conveniently obtained with a single conventional gas dilution system, diluters 23, 25 are each preferably constructed from conventional diluters placed in series. Such diluters 23, 25 may, for example, include a small sampling tube introduced into, and in alignment with, laminar flowing carrier gas and entrained particles to tap off a portion of the flowing gas stream within the cross sectional area of such sampling tube. In the preferred embodiment of the present invention, model 3302 diluters manufactured by TSI, Inc. are employed in dilution ratios of 20:1 and 100:1. At the outlet 24 of the initial diluter 23, the flow rate of carrier gas may be maintained at approximately the same flow rate as at the input (i.e., approximately 5 liters per minute) by the introduction of additional flowing carrier gas in the diluting process. Similarly, at the output 26 of the diluter 25, the flow rate of carrier gas (with entrained particles in concentration about 2000 times less than at the input of the initial diluter 23) may be maintained at approximately the same flow rate as at the input (i.e., approximately 5 liters per minute) by the introduction of additional flowing carrier gas in the diluting process. The additional carrier gas for each of the diluters 23, 25 may be supplied from the common gas supply 12 to reduce effects of pressure variations along the course of the flowing gas stream.

The output stream 26 of diluter 25 is divided into three separate flowing gas streams 27, 33, 39 by a standard type four-way-cross connector 28. The first stream 27 is supplied at a fixed flow rate to the particle counter 29 (e.g., a condensation nucleus counter) which monitors the particle size distribution and concentration in the output stream 26 of the diluter 25. Such particle counter may be a conventional condensation nucleus counter such as model 3760 manufactured by TSI, Inc. The particle counter 29 includes a flow control device (not shown) which maintains the gas inflow at a fixed rate (e.g., approximately 1.5 liters per minute for the TSI model 3760).

The second stream 33 is supplied to the input of the process chamber 14 being analyzed, at a flow rate that is controlled by needle valve 31. This valve, or additional valves (not shown) in the second stream 33 may be controlled selectively to inject particles at a precise time during operating sequences in which process chamber 14 is not being used to process an actual semiconductor wafer. A final level of dilution may be provided by adding carrier gas 37 directly to the process chamber 14 in combination with the flowing gas stream 35 from the outlet of the needle valve 31. To reduce errors resulting from variations in gas pressures in the system, the gas input 37 may be derived from the common gas supply 12 that also supplies the disperser 13 and the diluters 23, 25. Of course, the gas supply 12 may contain one or more flow controllers (not shown) to regulate collectively or independently the flows of carrier gas to the disperser 13, diluters 23, 25 and chamber 14.

The supply of particles entrained within the gas stream 33 to the process chamber 14 may be initiated by a valve 19 connected to control the flowing stream 33 supplied to the needle valve 31 in on-off manner. The actual particle concentration in the process chamber 14 is determined by the setting of needle valve 31, or other suitable flow controller that controls the desired flow of carrier gas and entrained particles into the process chamber 14, and by the flow of carrier gas 37.

In addition to controlling the rate of particle-laden gas flow into the process chamber 14, the needle valve 31 adjusts the pressure of the gas from ambient pressure to the subatmospheric pressure of the process chamber 14. Most elements of the present invention operate at or near ambient pressure because particles are easier to transport and there are fewer particle losses due to, e.g., the significant increase in gravitational settling and inertial losses in conduit bends which occur at lower pressures. The needle valve 31, therefore, should be disposed as close to the process chamber 14 as possible so that as much particle transport as possible is performed at ambient pressure.

Alternatively, the needle valve 31 may be replaced by a conventional sharp-edged orifice. The diameter of such a sharp-edged orifice maybe altered in order to vary gas flow rates and levels of pressure adjustment. In another alternative embodiment, a long, thin tube may be used in place of needle valve 31 in order to achieve the desired pressure drop to subatmospheric levels. Again, any device used to adjust the pressure should be disposed as close to the process chamber 14 as possible to avoid particle loss in the gas flow before entering the process chamber 14, for reasons as described above.

The third stream 39 includes the remaining portion of the output stream 26 that is not directed to the particle counter 29 or to the process chamber 14. This output stream 39 is filtered by a filter 41 of low pressure drop to remove the particles, and is then processed to retrieve or otherwise neutralize the carrier gas in the output stream 26. Since the powder disperser 13 typically operates at a higher flowrate than needed by the particle counter 29 (e.g., condensation nucleus counter) and by the chamber 14, the filter 41 vents any unneeded gas flow at ambient pressure and avoids a possible build-up of unneeded gas at the inlet to particle counter 29. This helps assure that the pressure at the inlet to particle counter 29 will not vary appreciably from ambient pressure as a requirement for the particle counter 29 (i.e., a condensation nucleus counter) to operate properly.

Counter 16 is connected to the outlet 43 of process chamber 14 to which conventional vacuum pumping equipment is connected in order to draw the gas stream out of process chamber 14 and into counter 16. This counter 16 determines the particle size distribution and concentration of the gas stream flowing out of the chamber 14 through outlet 43. The particle size distribution and concentration data from counter 16, and the particle size distribution and concentration data from counter 29, may be compared to determine the number of particles deposited or lodged in the process chamber 14 as a function of manufacturing process parameters such as pressure, flowrate, temperature, process chamber geometry, particle size, and gas composition. In the preferred embodiment of the present invention, counter 16 is a VACULAZ sensor (manufactured by Particle Measuring Systems, Inc. of Boulder, Colo.) which sizes and counts particles by sensing pulses of radiant energy produced by particles during transit through a laser beam. Alternatively, a test semiconductor wafer may be positioned in the process chamber 14 in order to determine the number of particles deposited on the semiconductor wafer as a function of such manufacturing parameters in a manner as later described herein.

Throughout the system illustrated in FIG. 1, the flowing gas streams 19, 21, 24, 26, 27, 33, 35, 43 may be constrained within short lengths of stainless steel tubing and connectors that include rounded corners and smooth inner walls to inhibit the build up of electrostatic charge on particles, and to preclude formation of physical barriers to the substantially laminar flow of the gas streams with the substantially uniformly-distributed particles entrained within such gas streams.

Figure 2:
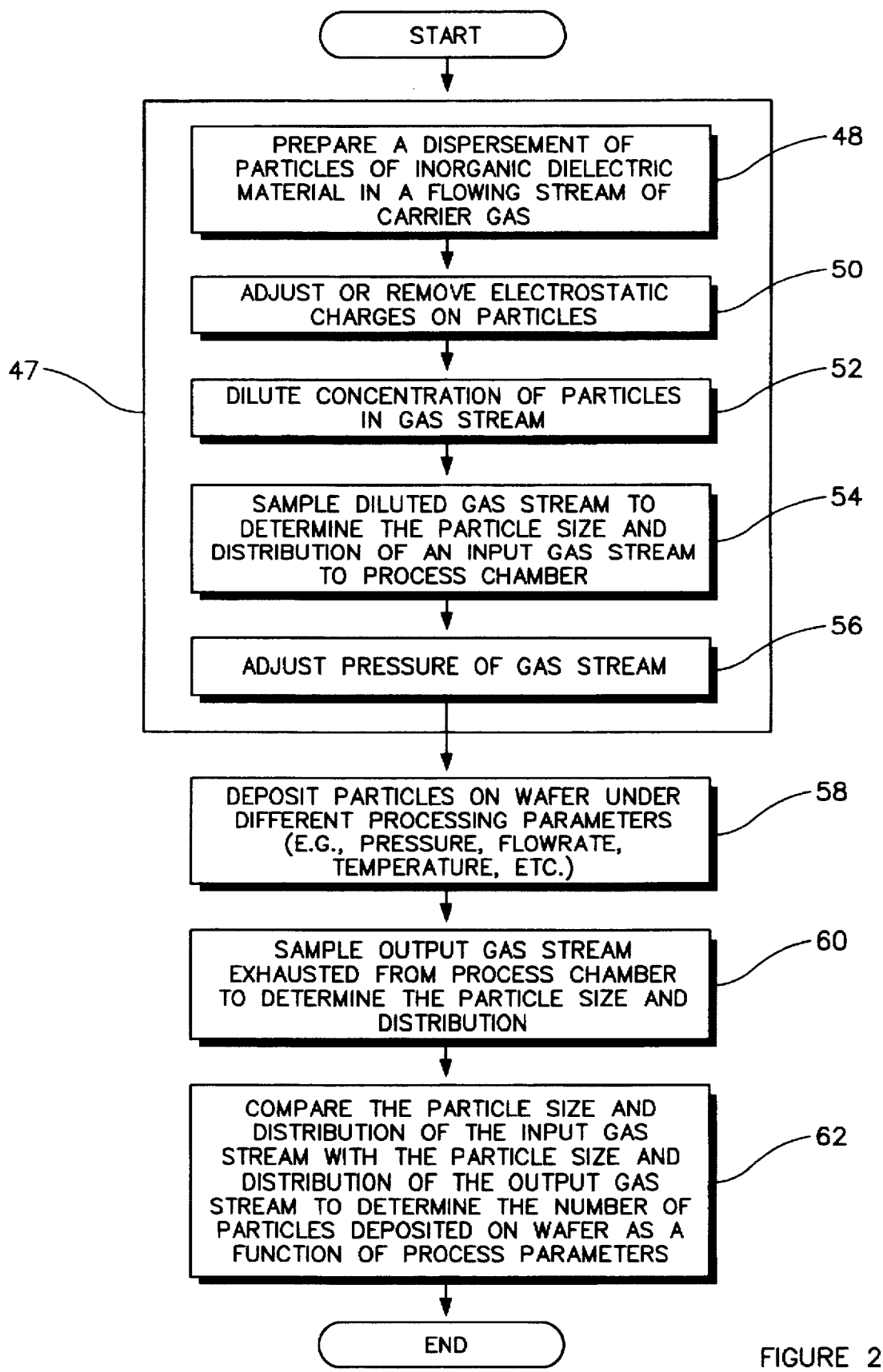
FIG. 2 is a flow chart illustrating the process of the present invention.

Referring now to the flow chart of FIG. 2, the method of the present invention operates on particles of an inorganic dielectric material such as silicon dioxide within a selected range of sizes (e.g. from approximately 0.15 microns to approximately 5.0 microns) that are entrained in a flowing gas stream which is then applied to a process chamber being analyzed. Analysis may determine the number of particles deposited on a semiconductor wafer during manufacture as a function of manufacturing process parameters such as pressure, flowrate, temperature, process chamber geometry, particle size, and gas composition.

Specifically, in a preferred embodiment, the powder disperser 13 prepares a dispersement 48 of such particles in a flowing stream of carrier gas for supply to the charge-altering device 18 which adjusts 50 any electrostatic charges on the particles in the flowing gas stream so that the charges are removed or substantially removed. Alternatively, the charge on the particles may be altered to exhibit net positive or negative charge, as desired. The diluters 23, 25 reduce the concentration 52 of particles in the flowing stream of carrier gas. Next, the particle counter 29 (e.g., a condensation nucleus counter) samples 54 a first portion 27 of the diluted stream 26 to determine the particle size distribution and concentration of an input gas stream to process chamber 14. A second portion 33 of the diluted stream 26 is supplied to needle valve 31 to adjust the pressure level 56 of the second stream 33 substantially to the pressure level of the chamber 14. The process chamber 14 is then supplied with the pressure-adjusted gas stream 35, and the particles lodge or deposit 58 on surfaces of the chamber or of a semiconductor wafer. The counter 16 samples 60 an output gas stream exhausted from process chamber 14 to determine the particle size distribution and concentration in the outlet stream of gas 43. The particle size distribution and concentration data from counter 29, and the particle size distribution and concentration data from counter 16 may then be compared in order to determine the number and sizes of particles lodged in the chamber or deposited on the test semiconductor wafer as a function of manufacturing process parameters such as pressure, flowrate, temperature, process chamber geometry, particle size, particle charge, and gas composition. Such comparison and subsequent analysis may be performed using conventional computational routines or computer programs.

Figure 3:
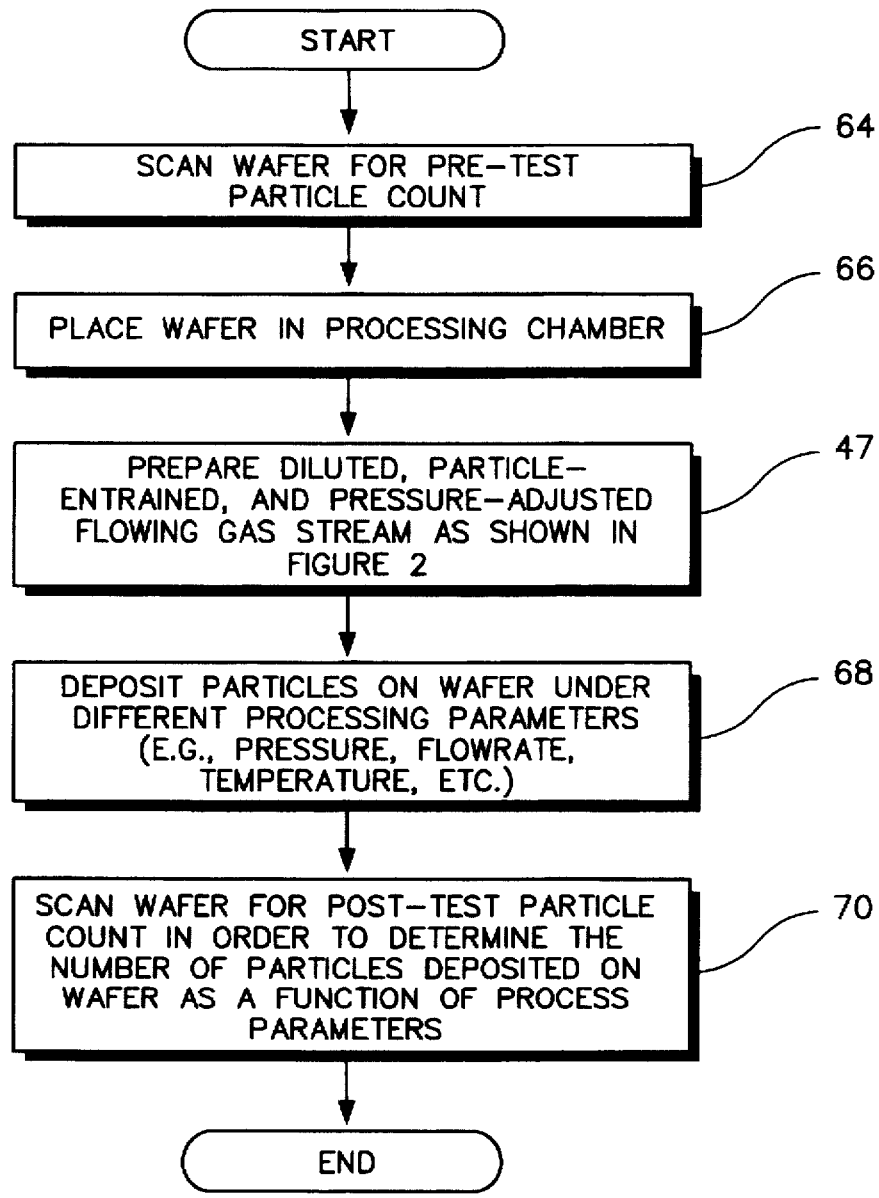
FIG. 3 is a flow chart illustrating an alternative embodiment of the process of the present invention.

Referring now to the flow chart of FIG. 3, an alternative embodiment of the method of the present invention utilizes a laser-scattering device that can count and size particles on a test semiconductor wafer. Such laser-scattering device may be a Surfscan 6200 model manufactured by Tencor, Inc. Specifically, a laser-scattering device scans 64 a wafer for the number of particles on the wafer before the wafer is placed 66 in the process chamber 14. Next, the overall method 47 is performed including preparing particles entrained in a flowing gas stream that are charge-adjusted, diluted, and supplied at reduced pressure in a flowing gas stream 35 in the same manner as described with reference to FIG. 2. Process chamber 14 is then supplied with gas stream 35, which deposits particles 68 on the wafer. A laser-scattering device scans 70 the surfaces of the test wafer for a post-test particle count in order to determine the number of particles deposited on the test wafer under manufacturing conditions as a function of manufacturing process parameters such as pressure, flowrate, temperature, process chamber geometry, particle size, particle charge, and gas composition.

Therefore, the system and method of the present invention operates on inorganic particles of dielectric material in known concentrations entrained within a stream of carrier gas that is introduced into a process chamber to determine its particle transport characteristics from an analysis of the particle count detected flowing out of the process chamber through the associated vacuum pumping system.

What is claimed is:

1. A method for testing of semiconductor manufacturing equipment comprising the steps of:

preparing a dispersement of particles in a first stream of carrier gas;

diluting the concentration of the particles in the first stream of carrier gas;

splitting the first stream to form second and third streams of carrier gas;

sampling the second stream of carrier gas to determine the particle size distribution and concentration of the second stream;

adjusting the pressure of the third stream to a selected pressure in the equipment under test;

supplying the equipment with the pressure-adjusted third stream of gas;

sampling an outlet stream of gas exhausted from the equipment to determine the particle size distribution and concentration of the outlet stream; and comparing the particle size distribution and concentration of the second stream with the particle size distribution and concentration of the outlet stream in order to determine the number of particles lodged within the equipment as a function of selected operating parameters of the equipment under test.

2. The method of claim 1 wherein the step of preparing a dispersement of particles in a firs stream of carrier gas further includes the step of:

adjusting electrostatic charge on the particles in the first stream of carrier gas.

3. The method of claim 1 wherein the selected operating parameters include at least one of pressure, flowrate, temperature, process chamber geometry, particle size, particle charge; and gas composition.

* * * * *